United States Patent
Yoneda et al.

(10) Patent No.: US 6,495,598 B1
(45) Date of Patent: Dec. 17, 2002

(54) PERFUSATE PREPARATION FOR OPHTHALMIC OPERATION

(75) Inventors: Toyoaki Yoneda, Osaka; Nobuhisa Naoi, Miyazaki; Hiroaki Miichi, Toyooka; Shigeru Nakamura, Toyooka; Toshinao Hata, Toyooka; Fumio Saito, Toyooka; Takeshi Ohnuma, Chuo-ku, all of (JP)

(73) Assignee: Ophtecs Corporation, Osaka (JP)

(*) Notice: Subject to any disclaimer, the term of this patent is extended or adjusted under 35 U.S.C. 154(b) by 0 days.

(21) Appl. No.: 09/807,739
(22) PCT Filed: Oct. 21, 1998
(86) PCT No.: PCT/JP98/04757
§ 371 (c)(1), (2), (4) Date: Apr. 18, 2001
(87) PCT Pub. No.: WO00/23048
PCT Pub. Date: Apr. 27, 2000

(51) Int. Cl.⁷ .................................. A61K 31/22
(52) U.S. Cl. ........................ 514/546; 514/912
(58) Field of Search ................... 514/546, 912

(56) References Cited

U.S. PATENT DOCUMENTS

| | | |
|---|---|---|
| 4,443,342 A | 4/1984 | Garabedian |
| 4,933,482 A | 6/1990 | Sayo et al. |
| 5,116,868 A | 5/1992 | Chen et al. |
| 5,292,774 A | 3/1994 | Hiraide et al. |
| 5,298,487 A | 3/1994 | Cheng et al. |
| 5,466,673 A | 11/1995 | Ohmori et al. |
| 506,892 A | 2/1997 | Ikejiri et al. |

FOREIGN PATENT DOCUMENTS

| | | |
|---|---|---|
| EP | 0517970 | 11/1991 |
| JP | 58-72515 | 4/1983 |
| JP | 2-191212 | 7/1990 |
| JP | 6-65061 | 3/1994 |
| JP | 6-99367 | 12/1994 |
| JP | 7-33601 | 2/1995 |
| JP | 7-97331 | 4/1995 |
| JP | 7-228532 | 8/1995 |
| JP | 11-5737 | 1/1999 |

OTHER PUBLICATIONS

The 36th Annual Meeting Program (The Retina Vitreous Society Of Japan) p. 201.
Ganka Rinsho IHO, vol. 92, No. 7, pp. 902–905 (1998).
Chem. Pharm. Bull., 41, p 1118 (1993).
WO96/00055 international Application published Under The Patent Cooperation Treaty Jan. 4, 1996.
WO87/03809 International Application Published Under The Patent Cooperation Treaty Jul. 2, 1987.

*Primary Examiner*—Zohreh Fay
(74) *Attorney, Agent, or Firm*—Sherman & Shalloway (57) ABSTRACT

A one-pack preparation of irrigating solution for ocular surgery of cataract, glaucoma or intraocular lens transplantation, which is excellent in the protection of ophthalmic tissues and endothelial cells during and after the operation and has a high in vivo stability. The preparation comprises an aqueous solution containing at least one compound selected from D-3-hydroxybutyric acid and water-soluble salts thereof, at least one compound selected from water-soluble bicarbonates, phosphoric acid and water-soluble phosphates, a water-soluble calcium salt, and a water-soluble magnesium salt.

8 Claims, 5 Drawing Sheets

(average±standard error, n=10)
*:$p<0.05$ (versus DMEM medium)

PERFUSATE PREPARATION FOR OPHTHALMIC OPERATION

This application is a 371 of PCT/JP98/04757 filed on Oct. 21, 1998.

1. Technical Field

The present invention relates to a preparation of irrigating solution for ocular surgery which may be used in the surgery of cataract, intraocular lens transplantation or glaucoma. More specifically, it relates to a preparation of irrigating solution which is suitable for protecting intraocular tissues, removing the substances left in the eye after the surgery by suction and preventing the surface of the corneal epithelium and the conjunctiva from drying in order to perform the surgery safely and effectively.

2. Background Art

Recently, development of ocular surgery methods for surgery of cataract, intraocular lens transplantation, glaucoma and the like has remarkably progressed. An irrigating solution which is used as a surgical adjuvant plays an important role in order to perform the above surgery safely and effectively. For example, when the periphery of the cornea is incised by a scalpel at the start of the surgery of cataract, the aqueous humor flows out from the anterior chamber immediately. Therefore, injection of an irrigating solution and a viscoelastic substance is indispensable for protecting intraocular tissues and cells and for maintaining the space of the anterior chamber. Further, when the irrigating solution is present in the eye at the time of breaking the opaque crystalline lens into pieces and extracting them, the pieces can be removed smoothly by suction. The irrigating solution is also used for preventing the surfaces of the cornea and the conjunctiva from drying during operation.

Some important points in the preparation for achieving such application purposes of the irrigating solution are as follows: (1) the osmotic pressure and pH of the preparation must be physiologically harmonized with the intraocular tissues and the corneal endothelial cell; 2) the essential compounds of aqueous humor components such as inorganic salts, energy sources and cell-activators must be added; 3) the preparation must be biologically safe; and 4) the preparation must be able to be preserved at room temperature for the long term.

One of preparation of irrigating solution for ocular surgery which are currently available in Japan's market is a commercial product containing oxyglutathione as a cell-activator, and another commercial product having a bicarbonate ion-based buffer system has already been practically used. However, since these are a two-pack preparation which requires two types of solutions to be mixed prior to use or a preparation which contains no ingredients effective for protecting the corneal endothelial cell, they have not a few problems to be solved with regard to stability, simplicity at the time of use and efficacy as a preparation.

A preparation of irrigating solution for ocular surgery which is composed essentially of 3-hydroxybutyric acid as an energy source is disclosed in the specifications of U.S. Pat. Nos. 5,116,868 and 5,298,487. However, the preparations described in the specifications do not contain bicarbonate ions necessary to sustain the function of the corneal endothelial cell. The disclosed reasons why the preparation does not have to contain the bicarbonate ions in advance are that when the bicarbonate ions exist in the preparation, the pH of the preparation fluctuates due to a $CO_2$ partial pressure, whereby the preparation becomes unstable, and that 3-hydroxybutyric acid generates $CO_2$ through metabolism and the $CO_2$ changes into the bicarbonate ions which are therefore supplied automatically. In addition, sodium acetate, which is generally said to be absent in human aqueous humor, is contained in the above preparation.

D-3-hydroxybutyric acid or its salts used as active ingredients in the present invention are known to be biological substances existing in humans and most of other mammals, biosynthesized through an oxidation process of fatty acids in the liver, and carried into the cornea as well as peripheral tissues out of the liver by blood to be utilized as an efficient energy source (refer to Lehninger, New Biochem., 2nd Ed., p625, 1993 and NATURE, No.4, 841, p597, 1962). It is also known that the substances are much more useful for corneal tissues as an energy source than glucose (refer to TRANSPLANTATION, 57, p1778–1785, 1994).

D-3-hydroxybutyric acid or its salts are oxidized in the TCA cycle of these tissues to produce ATP and are eventually converted into carbon dioxide and water (refer to NATURE, No.4841, p597, 1962).

As for the application of D-3-hydroxybutyric acid and its salts to drugs, it has been reported that they are mixed into an infusion solution for supplying nutrients to patients in the accelerated state as to biological protein catabolism or those having an invaded body (refer to Japanese Patent Application Laid-Open No. 191212/1990).

It is disclosed in GANKA RINSHO IHO, Vol.92, No.7 (1998), p902–905, that the influence of an intraocular irrigating solution containing β-hydroxybutyrate on the retinas has been studied on an electroretinogram (ERG) using the retinas extracted from rabbits and that the intraocular irrigating solution sustains retinal functions which are equal to or more than the market product BSS PLUS (registered trademark) does. However, the D-form of β-hydroxybutyrate is not disclosed in this report, and only the influence of β-hydroxybutyrate on the retinas is disclosed.

In addition, the Proceeding 201 of the 36th Meeting of the Retina Vitreous Society of Japan held on Jul. 24–26, 1997, discloses that the influence of a newly formulated intraocular irrigating solution containing sodium D-β-hydroxybutyrate on the retinas was studied on an ERG using the retinas extracted from rabbits and that the newly formulated intraocular irrigating solution could sustain the ERG of a retinal in vitro sample which is equal to or more than BSS PLUS does.

However, the detailed composition of the above irrigating solution is not disclosed in this report, and only its influence on the retinas is disclosed.

DISCLOSURE OF THE INVENTION

It is an object of the present invention to provide a one-pack preparation of irrigating solution for ocular surgery of cataract, glaucoma or intraocular lens transplantation, which is excellent in the protection of ophthalmic tissues and endothelial cells during and after the operation and has a high in vivo stability.

It is another object of the present invention is to provide an intraocular preparation of irrigating solution having formulation stability in addition to the above excellent properties by adding inorganic ions, energy sources, isotonic agents, buffers, bicarbonate ions and stabilizers.

Other objects and advantages of the present invention will become apparent from the following description.

According to the present invention, the above objects and advantages can be attained by a one solution-pack preparation of irrigating solution for ocular surgery of cataract, glaucoma or intraocular lens transplantation, which comprises an aqueous solution containing:

(1) at least 0.1 mM but less than 500 mM of at least one compound selected from the group consisting of D-3-hydroxybutyric acid and water-soluble salts thereof as a D-3-hydroxybutyrate anion;
(2) at least 0.1 mM but less than 100 mM of water-soluble bicarbonate salts as a bicarbonate ion;
(3) at least 0.1 mM but less than 50 mM of at least one compound selected from the group consisting of phosphoric acid and water-soluble phosphate salts thereof as a phosphate ion;
(4) at least 0.01 mM but less than 50 mM of water-soluble calcium salts as a calcium ion; and
(5) at least 0.01 mM but less than 50 mM of water-soluble magnesium salts as a magnesium ion.

PREFERRED EMBODIMENT OF THE INVENTION

The preparation of the present invention will be described in detail hereinafter.

As for the absolute configuration at the $C_3$ position in the chemical structural formula of 3-hydroxybutyric acid, there is a group of a D-form, a D,L-form and an L-form. Of these, in the present invention, the D-form is used to maximize the effectiveness of a formulation of irrigating solution for ocular surgery. This is because when the difference in activity based on the optical isomers with regard to an effect of activating the corneal endothelial cell, which is one of methods for evaluating the effectiveness of the preparation, is studied, activity is obtained with the D-form while it is hardly obtained with the L-form and because it is thought that when the D,L-form is used, the L-form may cause an adverse effect on the activity.

Since D-3-hydroxybutyric acid and its salts can be synthesized with ease and at high asymmetric yields by asymmetrically hydrogenating the ketone groups of an acetoacetic ester in the presence of a ruthenium-optically active phosphine complex as a catalyst and subjecting the ester to alkaline hydrolysis, the compounds can be obtained at relatively low cost (refer to Japanese Patent Publication No.99367/1990).

Preferable examples of the water-soluble salts of D-3-hydroxybutyric acid in the present invention include sodium salts, potassium salts, barium salts, magnesium salts, lithium salts, L-lysine salts, L-histidine salts and L-arginine salts. D-3-hydroxybutyric acid and its water-soluble salts can be used solely or in combination of two or more.

The term "water-soluble" as used in the present invention refers to the property of the compounds which enables the compounds to dissolve in the preparation of the present invention at the desired concentration required for the preparation.

According to the present invention, the concentration of D-3-hydroxybutyric acid and/or its water-soluble salts in the aqueous solution preparation is at least 0.1 mM but less than 500 mM, preferably at least 1 mM but less than 200 mM, and more preferably at least 5 mM but less than 100 mM.

In the present invention, the addition of bicarbonate ions exerts a remarkable influence on a cornea-swelling-inhibiting effect, which is one of important indexes for sustaining corneal functions. Actually, when the corneo-scleral pieces extracted from rabbits were incubated by using a preparation containing bicarbonate ions and a preparation containing no bicarbonate ions, respectively, and changes in the corneal thicknesses were measured, the preparation containing such ions (the present invention) restored the cornea to a nearly normal condition, whereas the preparation containing no such ions accelerated the corneal swelling, proving that it was lacking in the effect of protecting the cornea. Further, the above was also true in an in vivo experiment using the eyes of rabbits; that is, the preparation containing such ions (the present invention) restored the cornea to a normal condition, whereas the preparation containing no such ions accelerated the corneal swelling.

In consideration of the above facts, bicarbonate ions must be contained in the D-3-hydroxylutyric acid-containing preparation of the present invention.

Preferred examples of the water-soluble bicarbonate salts include sodium bicarbonate and potassium bicarbonate.

The concentration of the water-soluble bicarbonate salts is at least 0.1 mM but less than 100 mM, preferably at least 1 mM but less than 60 mM, and more preferably at least 10 mM but less than 60 mM, as water-soluble bicarbonate ions ($HCO_3^-$).

The preparation of the present invention contains phosphate ions, which are derived from phosphoric acid or water-soluble phosphate salts. The phosphate ions are preferably derived from a phosphate-based buffer which comprises water-soluble phosphate salts such as disodium hydrogen phosphate, sodium dihydrogen phosphate, dipotassium hydrogen phosphate and potassium dihydrogen phosphate. The phosphate-based buffer is present as a component of the human aqueous humor. The concentration of the phosphate ions is at least 0.1 mM but less than 50 mM, preferably at least 0.5 mM but less than 30 mM, and more preferably at least 1 mM but less than 10 mM.

The preparation of the present invention further contains calcium salts. The calcium salts may be added to the preparation of the present invention as salts comprising the D-3-hydroxybutyrate ions, bicarbonate ions or phosphate ions as described above and calcium ions or as other water-soluble salts. Preferable examples of such other water-soluble salts include calcium chloride and calcium glucuronate. The calcium salts can be used solely or in combination of two or more.

The concentration of the water-soluble calcium salts is at least 0.01 mM but less than 50 mM, preferably at least 0.1 mM but less than 20 mM, more preferably at least 0.5 mM but less than 10 mM, as calcium ions.

The preparation of the present invention further contains water-soluble magnesium salts. The magnesium salts may be added to the preparation of the present invention as salts comprising the D-3-hydroxybutyrate ions, bicarbonate ions or phosphate ions as described above and magnesium ions or as other water-soluble salts. Preferable examples of such other water-soluble salts include magnesium chloride and magnesium sulfate.

The concentration of the water-soluble magnesium salts is at least 0.01 mM but less than 50 mM, preferably at least 0.1 mM but less than 20 mM, and more preferably at least 0.5 mM but less than 10 mM, as magnesium ions.

As for the additives to the preparation of irrigating solution in the present invention, inorganic salts present in human aqueous humor, glucose as other energy source, isotonic agents and buffers for harmonizing the osmotic pressure and the pH with the intraocular tissues and the endothelial cells, and stabilizers for preparations and the like are preferably used as appropriate.

As the inorganic salts and isotonic agents used in the present invention, inorganic salts such as alkaline metal salts, e.g., sodium chloride and potassium chloride, and isotonic agents such as carbohydrates, e.g., mannitol, sorbitol, xylitol and dextran, are preferably used in addition to the above calcium salts and magnesium salts.

Those can be used solely or in combination of two or more. The concentration of the inorganic salts and that of the isotonic agents are preferably in the range of 0.1 to 1,000 mM. In addition, the osmotic pressure of the preparation is sustained preferably within the range of 270 to 350 mOsm.

As the buffers, citric acid, citrate salts, bicarbonate salts, acetate salts and boric acid-based buffers such as boric acid and sodium borate can be used in addition to the above water-soluble phosphate salts. The concentration of the buffers is preferably in the range of 0.1 to 50 mM.

The pH of the aqueous solution preparation of the present invention is preferably in the range of 6.8 to 8.2, within which no damages are caused on intraocular tissues and cells and which is required to sustain those functions. Further, a pH of 7.2 to 8.0 is more preferably because the range has been found to be permissible as an irrigating solution for ocular surgery as the result of the functionality and safety tests using the eyes of rabbits.

In the present invention, although the main energy source for the preparation of irrigating solution is D-3-hydroxybutyic acid, glucose may also be added as an auxiliary sub-energy source. The concentration of glucose is preferably in the range of 0.1 to 50 mM.

As the stabilizer, water-soluble citrate salts are preferably used. Preferable examples of the water-soluble citrate salts include citric acid, and its sodium salts and potassium salts. Its concentration is preferably in the range of 0.01 to 50 mM, and more preferably in the range of 0.1 to 10 mM, as citrate ions.

The required amounts of such main components and additives are dissolved in distilled water in turn, the pHs of the solutions are adjusted by diluted hydrochloric acid or a diluted alkaline solution, and the resulting solutions can be each preserved in a transparent glass or plastic bottle fitted with a stopper as one-pack preparations. The thus-prepared preparations were preserved at 40° C. and a humidity of 75% for 6 months, and the sample after the 6-month preservation was. the same as the sample at the start of the test in terms of appearance and osmotic pressure. As for pH, on the other hand, when the concentration of citric acid or its salts is set to be in the rage of preferably 0.01 to 50 mM, more preferably 0.1 to 10 mM, the pH of the preparation at the start of the test, which is 7.3 to 7.4, is in the range of 7.4 to 7.8 at the end of the above preservation, indicating that a change in the pH of the solution is small and that a stable irrigating solution can be obtained even when bicarbonate ions are present.

EXAMPLES

The following examples are given to further illustrate the present invention. However, it should be understood that the present invention is not limited by these examples.

Example 1

Irrigating solution No.1 (Example) and No.2 (Comparative Example) for testing were prepared by dissolving the predetermined amounts of the components listed in Table 1 in turn in the order they were listed and, finally, sodium D-3-hydroxy butyrate (to be referred to as "D-3-HBA" hereinafter) in distilled water so as to adjust the total amounts of the solutions to be 1 liter; adjusting the pHs of the solutions by diluted hydrochloric acid, and subjecting the solutions to aseptic filtration. The components of Commercial Products B (Comparative Solution 1) and M (Comparative Solution 2) used as additional Comparative Examples and the concentrations of the components are shown in Table 1.

TABLE 1

(mM)

| Component | Solution No.1 | Solution No.2 | Comparative Solution 1 | Comparative Solution 2 |
|---|---|---|---|---|
| NaCl | 100.3 | 100.0 | 122.2 | 112.9 |
| KCl | 5.1 | — | 5.08 | 4.8 |
| $MgCl_2$ | 1.0 | 1.0 | 0.98 | — |
| $CaCl_2$ | 1.1 | 2.0 | 1.05 | 1.2 |
| $K_2HPO_4$ | — | 5.0 | — | — |
| $Na_2HPO_4$ | 3.0 | 5.0 | 3.0 | — |
| sodium citrate | 0.34 | 10.0 | — | 3.4 |
| $NaHCO_3$ | 25.0 | — | 25.0 | 25.0 |
| sodium acetate | — | 20.0 | — | 4.4 |
| D-3-HBA | 20.0 | — | — | — |
| D,L-3-HBA | — | 10.0 | — | — |
| oxyglutathione | — | — | 0.30 | — |
| glucose | 5.0 | 5.5 | 5.11 | 8.3 |

Example 2

The preparation stability test of the D-3-HBA-containing solution No.1 of Example 1 was performed. Five bottles of the solution to be tested were prepared by charging 500 mL of the preparation into 600-ml transparent glass containers and capping the bottles. Those were preserved for 6 months in an instrument maintained at 40±0.5° C. and 75±5% humidity. As a result, no changes occurred in the appearances of the solutions, the insoluble umpurity test and the osmotic pressure. As for the pHs of the solutions, while they were 7.3 to 7.4 at the start of the preservation, they became 7.4 to 7.8 after the 6-month preservation, showing relatively small changes. Accordingly, it was found that the preparation could be preserved stably at room temperature for the long term.

Example 3

To confirm that the D-form isomer of 3-HBA was the most effective among the D-form, D,L-form and L-form isomers thereof, the cell-activating effect of each isomer was measured quantitatively by using an incubated bovine corneal endothelial cell according to the following MTT assay-based method (Chem. Pharm. Bull., 41, 1118, 1993).

Figure 1:
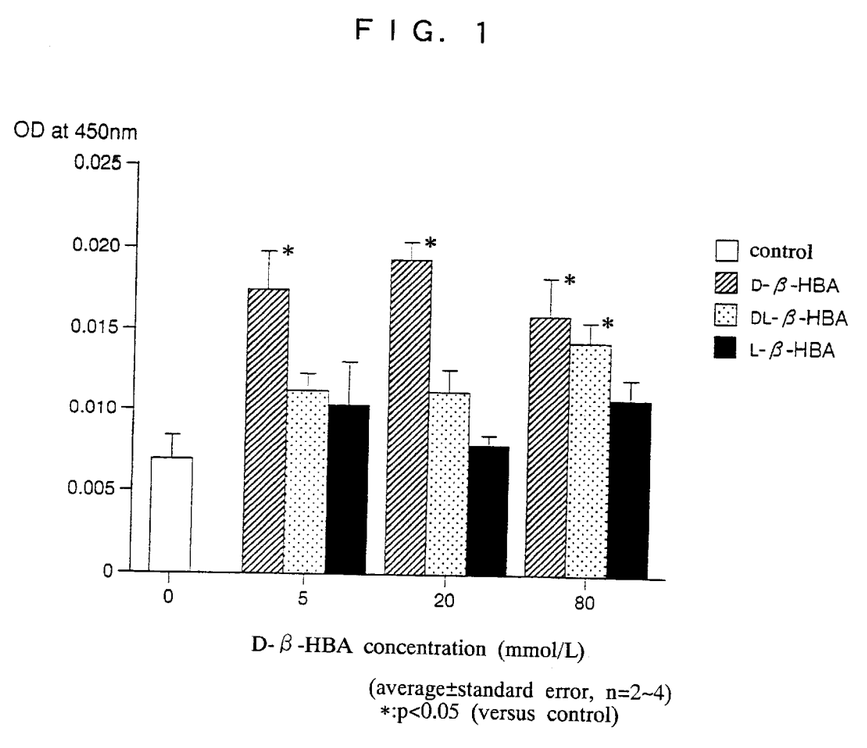
FIG. 1 shows the comparison of the cell-activating effects by optical isomers of 3-hydroxybutyric acid (3-HBA).

The D-form, D,L-form and L-form of D-3-HBA were dissolved in the DULBECCO's MEM salt incubation media at concentrations of 0 (control), 5 and 20 mM, respectively, and the resulting solutions were injected into a 24-well collagen-coated plate implanted ($4\times10^4$ cell/ml) with a pre-incubated bovine corneal endothelial cell and then incubated for 48 hrs. After the incubation, 50 µl of cell-counting kit (product of DOJIN KAGAKU Ltd.) was added to each well to develop colors, and absorbance at 450 nm was measured by using each supernatant. The results are shown in FIG. 1.

As for the cell-activating effects of the D-form, D,L-form and L-f form, the cells incubated in the presence of D-3-HBA were the most active at any concentrations, and the optimum concentration was 20 mM. The L-form did not show a significant difference in activity at any concentrations, as compared with the control group (containing no HBA). The D,L-form did not show a significant difference at concentrations of 5 mM and 20 mM, as compared with the control group.

Example 4

Using four types of the testing irrigating solutions described in Example 1, i.e., Solutions No.1 and No.2 and Comparative Solutions 1 and 2, their cornea-protecting effects were compared with one another by performing an in vitro experiment.

Sclerocorneas (5 pieces for each of the four testing solutions, 20 pieces in total) having about-5-mm-wide sclerae around the corneas were extracted from mature rabbits and incubated in the testing irrigating solutions at 36° C. for 5 hours. The corneal thicknesses were measured by an ultrasonic pachymeter (DGH-500 PACHETTE, a product of DGH TECHNOLOGY).

Figure 2:
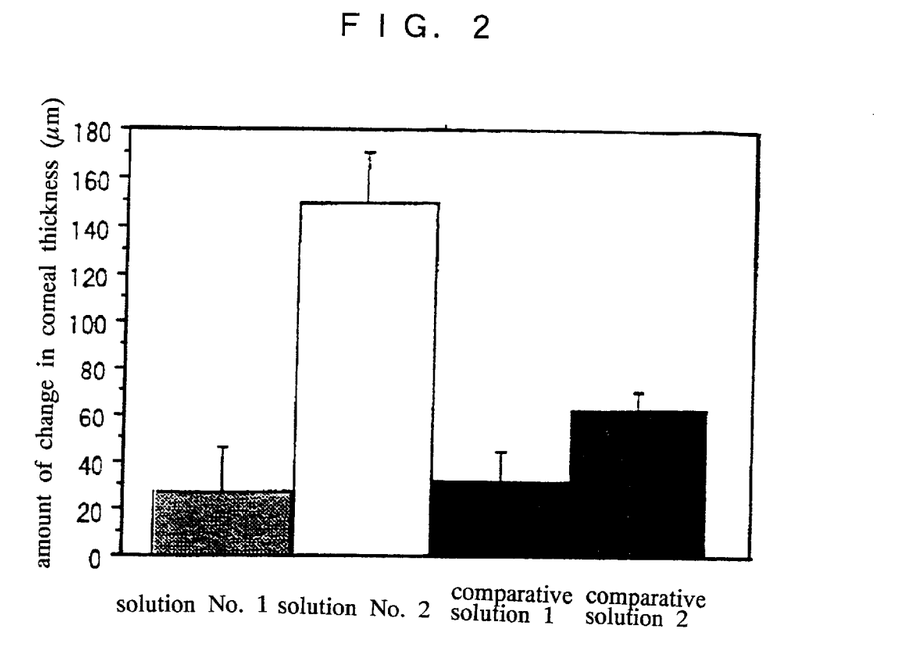
FIG. 2 shows the protection effects (in vitro experiments) of the solution of the present invention and comparative solutions on the corneas.

The amounts of changes in the corneal thickness (=the corneal thickness before incubation—the corneal thickness after 5-hr incubation) after the 5-hr incubation of each testing solution are shown in FIG. 2.

Solution No.1 containing D-3-HBA and bicarbonate ions showed a remarkable cornea-protecting effect, as compared with Solution No.2 containing no bicarbonate ions. Further, Solution No.1 also showed a cornea-swelling-inhibiting effect which is the same as or greater than those of commercially available Comparative Solutions 1 and 2.

Example 5

Four types of the testing irrigating solutions described in Example 1, i.e., Solutions No.1 and No.2 and Comparative Solutions 1 and 2, were also investigated for their effects to the corneal thickness by an in vivo experiment in which the solutions were irrigated in the anterior chambers of Dutch rabbits (male and female weighing 1.9 to 2.9 kg).

Experiments were performed in rabbit, anesthetized with intramuscular xylazine hydrochloride ("celactal®", a product Bayer AG.,) and ketamine hydrochloride ("ketalar®", a product of Sankyo Co. Ltd,.). A 3.2-mm-wide incision was made around the corneas of the left and right eyes of each rabbit using a scalpel for ocular surgery. Subsequently, 18-gauge injection needles having a rounded tip were inserted in the anterior chambers through the incisions, and the four types of testing irrigating solutions were allowed to irrigate at a flow rate of 10 ml/min for 120 minutes. The amount of change in the corneal thickness by each solution was measured by the above ultrasonic pachymeter before the start of the irrigation and every 30 minutes after the start of the irrigation under local anesthesia maintained by giving eye drops of a 0.4% oxyprocaine hydrochloride solution. The amounts of changes in the corneal thicknesses with time are shown in FIG. 3.

Figure 3:
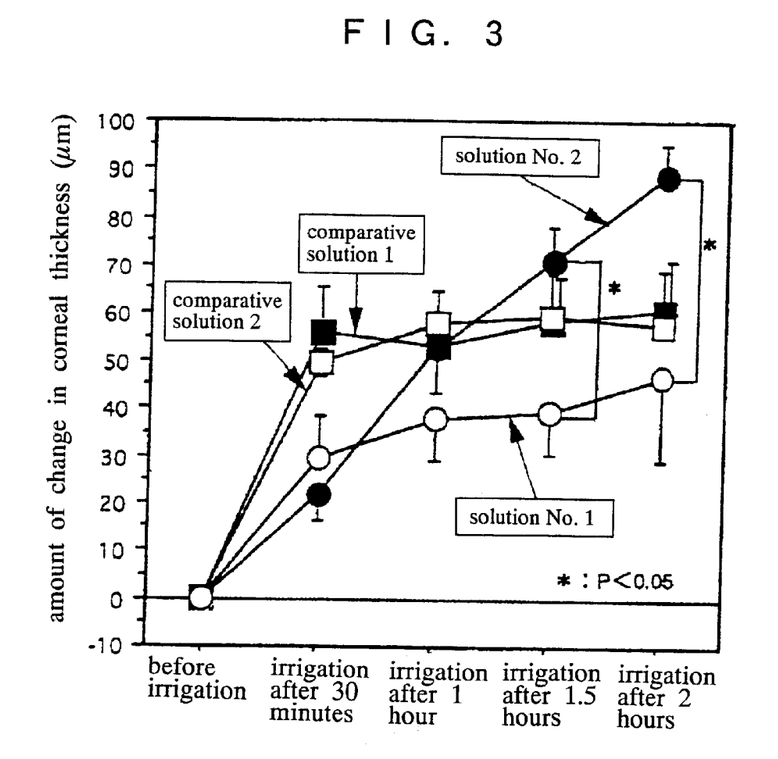
FIG. 3 shows the amount of change in the corneal thickness with time by each of the above solutions.

As a result, FIG. 3 shows that Solution No.1 containing D-3-HBA and bicarbonate ions is a preparation of irrigating solution which causes a significantly small change in the corneal thickness and which has an excellent cornea-protecting effect as compared with Solution No.2 containing no bicarbonate ions and with Comparative Solutions 1 and 2, as in the result of the in vitro experiment of Example 4.

Example 6

As an invasive model assuming a phacoemulsification and aspiration method used as a surgical method of cataract, incubated bovine corneal endothelial cells damaged by ultrasound were subjected to an experiment for examining the recovery of their barrier function.

Using the incubated bovine corneal endothelial cells damaged by ultrasound, the barrier function-recovering effects of D-3-HBA and oxyglutathione were subjected to an experiment in accordance with the following procedure.

Figure 4:
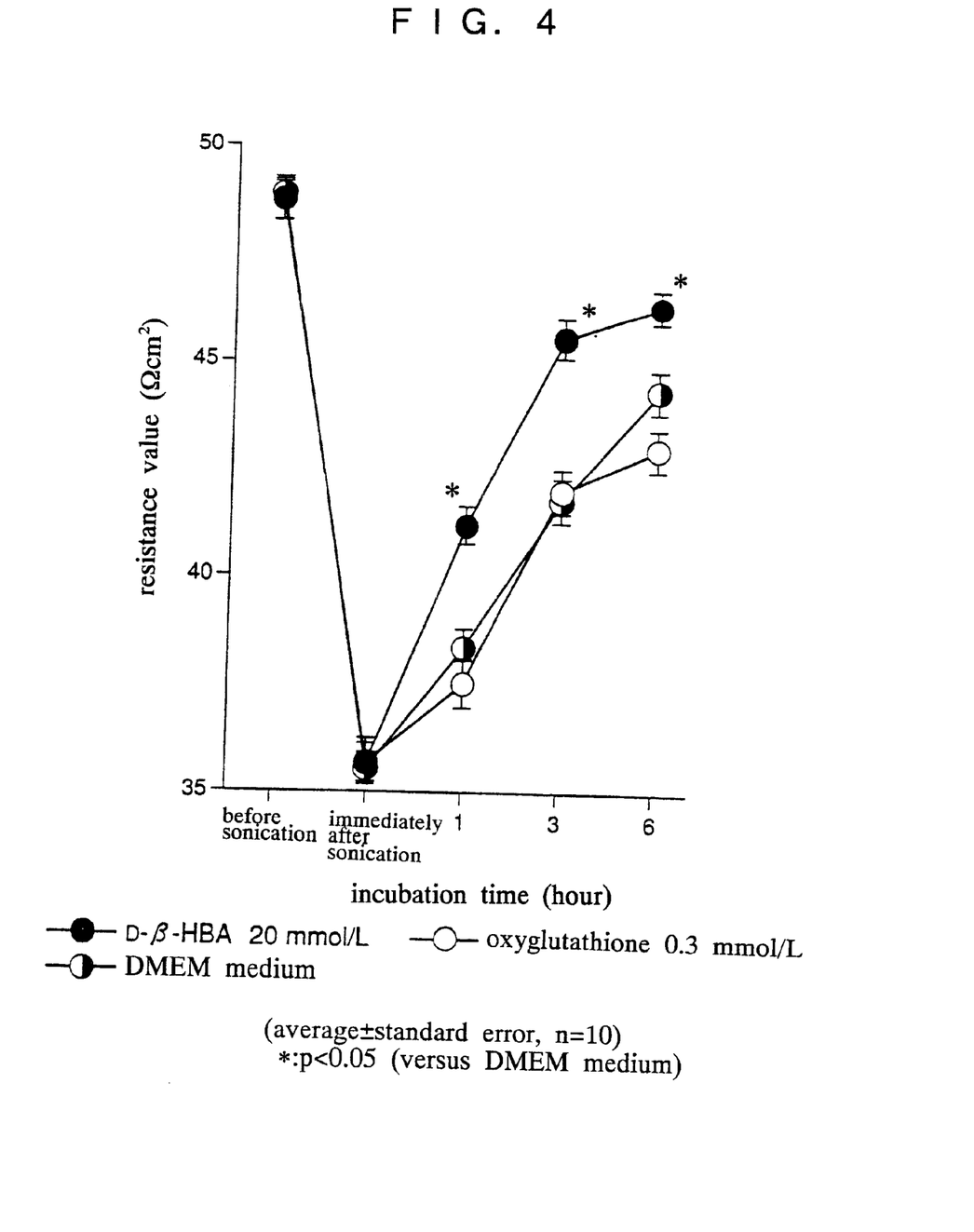
FIG. 4 shows the recovery effects of D-3-HBA and oxyglutathione on an cultured bovine corneal endothelial cell which is damaged.

The monolayer of cultured bovine corneal endothelial cells on a filter, which had been damaged by sonication to the cells at 92 W/cm² three course at intervals of 0.1 sec, was incubated in DULBECCO's MEM medium (with 10% of embryonic bovine serum) containing 20 mM of D-3-HBA or 0.3 mM of oxyglutathione. FIG. 4 shows the results of measuring the degrees of recovery of the barrier function by using a change in the electrical resistance value of the endothelial layer with time as an index.

The monolayer in the medium containing D-3-HBA showed an electrical resistance value closer to the value before the irradiation of ultrasound at any observation time than those in the MEM medium containing oxyglutathione and the MEM medium containing neither D-3-HBA nor oxyglutathione, and it showed a quick recovery effect of the barrier function.

Example 7

Irrigating solution No.1 (Example) and solutions No.3, No.4 and No.5 (Comparative Examples) for testing were prepared by dissolving the predetermined amounts of the components listed in Table 2 and, finally, D-3-HBA so as to adjust the total amounts of the aqueous solutions to be 1 liter; adjusting the pHs of the solutions by diluted hydrochloric acid, and subjecting the solutions to aseptic treatment.

TABLE 2

| | | | | (mM) |
| --- | --- | --- | --- | --- |
| | containing bicarbonate salts | | containing no bicarbonate salts | |
| Solution No. | 1 | 3 | 4 | 5 |
| D-3-HBA | 20 | 0 | 0 | 20 |
| NaCl | 100.3 | 122.0 | 145.4 | 123.7 |
| KCl | 5.1 | 5.1 | 5.1 | 5.1 |
| Na$_2$HPO$_4$ | 3.0 | 3.0 | 3.0 | 3.0 |
| sodium citrate | 0.34 | 0.34 | 0.34 | 0.34 |
| MgCl$_2$ | 1.0 | 1.0 | 1.0 | 1.0 |
| CaCl$_2$ | 1.1 | 1.1 | 1.1 | 1.1 |
| NaHCO$_3$ | 25.0 | 25.0 | — | — |
| glucose | 5.0 | 5.0 | 5.0 | 5.0 |

Dutch rabbits (male and female weighing 1.9 to 2.9 kg) were used for an experiment. Experiments were performed in rabbit, anesthetized with intramuscular xylazine hydrochloride ("celactal®", a product Bayer AG.,) and ketamine hydrochloride ("ketalar®", a product of Sankyo Co. Ltd,.) through intramuscular injection, a 3.2-mm-wide incision was made corneas limbusing a scalpel for ocular surgery.

Subsequently, 18-gauge injection needles having a rounded tip were inserted in the anterior chambers through the incisions, and the irrigating solutions were allowed to irrigate at a flow rate of 10 ml/min for 90 minutes. After the irrigation, the incisions were sewed up once by a sewing needle with a suture. The corneal thicknesses were measured by the ultrasonic pachymeter used in Example 4 before and during the perfusion (at intervals of 30 minutes).

Figure 5:
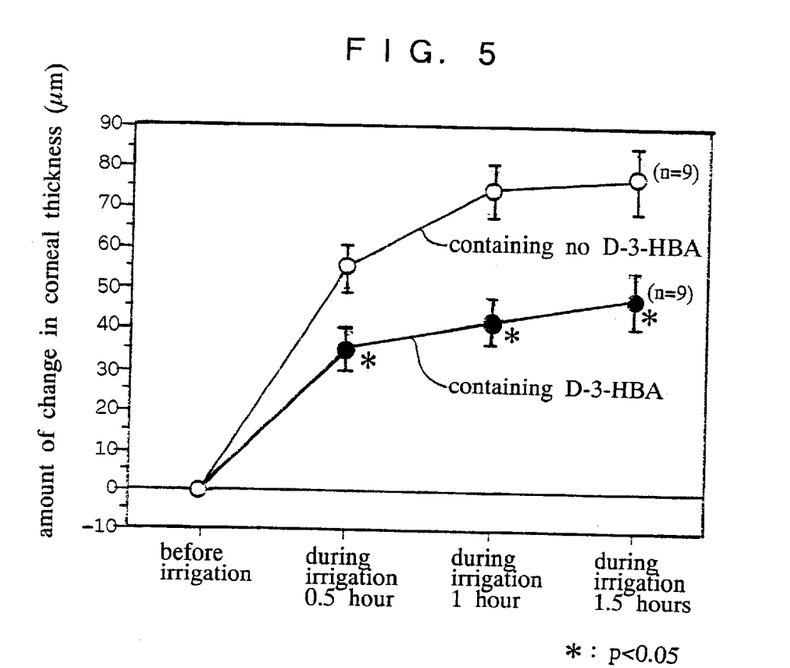
FIG. 5 shows the amount of change in the corneal thickness with time by a bicarbonate salts-containing preparation with or without D-3-HBA.
Figure 6:
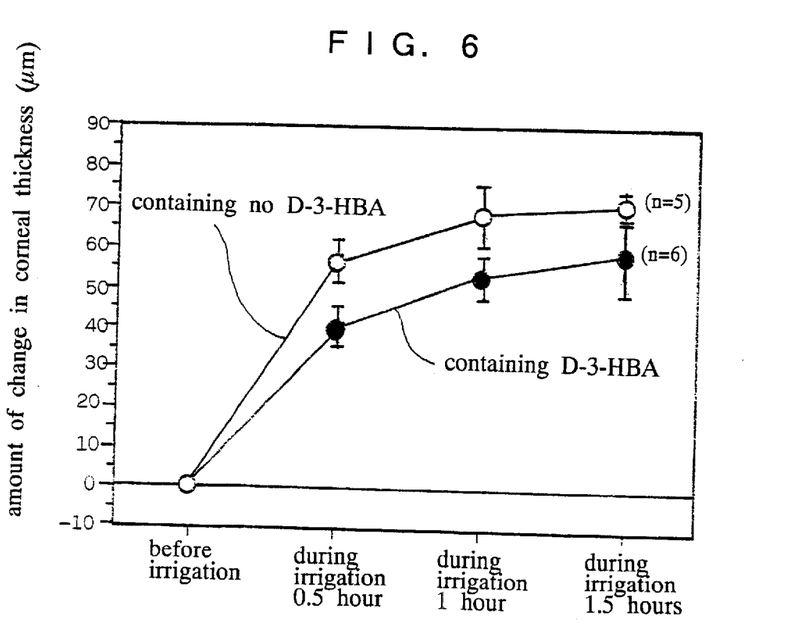
FIG. 6 shows the amount of change in the corneal thickness with time by a bicarbonate salts-free preparation with or without D-3-HBA.

The effect of D-3-HBA to keep a change in the corneal thickness small by adding D-3-HBA and bicarbonate ions to the intraocular irrigating solutions was significant (FIG. 5). On the other hand, in the case of the preparations in which the bicarbonate ions were not added to the intraocular irrigating solutions, the effect of keeping the change in the corneal thickness small by D-3-HBA was not significant (FIG. 6).

As described above, according to the present invention, by using sodium D-3-hydroxybutyric acid and/or salts thereof, bicarbonate ions, phosphate ions, calcium ions, magnesium ions and, in some cases, citrate ions in combination as an energy source, a preparation of irrigating solution for ocular surgery could be prepared that is highly safe as an irrigating solution for ocular surgery, has an excellent effect of protecting ocular tissues including corneal endothelial cells and an excellent effect of recovering physically damaged ocular tissues, and is stabilized by adding inorganic salts, isotonic agents, glucose, buffers and stabilizers.

What is claimed is:

1. A one solution-pack preparation of irrigating solution for ocular surgery of cataract, glaucoma or intraocular lens transplantation, which comprises an aqueous solution containing:

(1) at least 0.1 mM but less than 500 mM of at least one compound selected from the group consisting of D-3-hydroxybutyric acid and water-soluble salts thereof as a D-3-hydroxybutyrate anion;

(2) at least 0.1 mM but less than 100 mM of water-soluble bicarbonate salts as a bicarbonate ion;

(3) at least 0.1 mM but less than 50 mM of at least one compound selected from the group consisting of phosphoric acid and water-soluble phosphate salts thereof as a phosphate ion;

(4) at least 0.01 mM but less than 50 mM of water-soluble calcium salts as a calcium ion; and (5) at least 0.01 mM but less than 50 mM of water-soluble magnesium salts as a magnesium ion.

2. The preparation of claim 1, wherein the water-soluble salts of D-3-hydroxybutyric acid are selected from the group consisting of the sodium salts, potassium salts, barium salts, magnesium salts, lithium salts, L-lysine salts, L-histidine salts and L-arginine salts of D-3-hydroxybutyric acid.

3. The preparation of claim 1, wherein the water-soluble bicarbonate salts are sodium bicarbonate or potassium bicarbonate.

4. The preparation of claim 1, wherein the water-soluble phosphate salts are selected from the group consisting of sodium dihydrogen phosphate, disodium hydrogen phosphate, potassium dihydrogen phosphate and dipotassium hydrogen phosphate.

5. The preparation of claim 1, wherein the water-soluble calcium salts are selected from the group consisting of calcium chloride, calcium glycerophosphate and calcium glucuronate.

6. The preparation of claim 1, wherein the water-soluble magnesium salts are magnesium chloride or magnesium sulfate.

7. The preparation of claim 1, further containing water-soluble citric acid and/or salts thereof.

8. The preparation of claim 7, wherein the water-soluble citrate salts are sodium citrate or potassium citrate.

* * * * *